(12) United States Patent
Marczyk

(10) Patent No.: US 10,070,849 B2
(45) Date of Patent: Sep. 11, 2018

(54) MARKING ARTICULATING DIRECTION FOR SURGICAL INSTRUMENT

(75) Inventor: Stanislaw Marczyk, Stratford, CT (US)

(73) Assignee: Covidien LP, Mansfield, MA (US)

( * ) Notice: Subject to any disclaimer, the term of this patent is extended or adjusted under 35 U.S.C. 154(b) by 1040 days.

(21) Appl. No.: 12/694,746

(22) Filed: Jan. 27, 2010

(65) Prior Publication Data

US 2010/0217279 A1 Aug. 26, 2010

Related U.S. Application Data

(60) Provisional application No. 61/154,202, filed on Feb. 20, 2009.

(51) Int. Cl.
| | | |
|---|---|---|
| *A61B 19/00* | (2006.01) | |
| *A61B 17/00* | (2006.01) | |
| *A61B 90/90* | (2016.01) | |
| *A61B 90/92* | (2016.01) | |
| *A61B 90/94* | (2016.01) | |
| *A61B 34/00* | (2016.01) | |
| *A61B 90/00* | (2016.01) | |

(52) U.S. Cl.
CPC ........ *A61B 17/00234* (2013.01); *A61B 90/90* (2016.02); *A61B 90/92* (2016.02); *A61B 90/94* (2016.02); *A61B 34/70* (2016.02); *A61B 2017/003* (2013.01); *A61B 2090/0807* (2016.02); *A61B 2090/0811* (2016.02)

(58) Field of Classification Search
CPC . A61B 19/44; A61B 2019/4857; A61B 19/22; A61B 19/2203; A61B 2019/2234; A61B 2019/507; A61B 2019/5291
USPC .................................. 606/130; 600/424–429
See application file for complete search history.

(56) References Cited

U.S. PATENT DOCUMENTS

| | | | |
|---|---|---|---|
| 5,280,179 A | 1/1994 | Pryor et al. | |
| 5,649,021 A | 7/1997 | Matey et al. | |
| 5,855,583 A | * 1/1999 | Wang | B25J 9/1689 |
| | | | 318/568.11 |
| 5,876,325 A | * 3/1999 | Mizuno | A61B 1/00048 |
| | | | 600/102 |
| 6,161,033 A | 12/2000 | Kuhn | |

(Continued)

FOREIGN PATENT DOCUMENTS

| | | |
|---|---|---|
| EP | 1 915 957 A2 | 4/2008 |
| WO | WO 02/051318 A1 | 7/2002 |

OTHER PUBLICATIONS

European Search Report for EP 10250296.0-2310 date of completion dated May 31, 2010 (5 pages).

*Primary Examiner* — Katherine Rodjom

(57) ABSTRACT

A surgical apparatus for guiding the movement of a surgical tool in relation to the surrounding anatomy of a patient includes a surgical tool having an articulation member. The apparatus also has an image capturing device, a monitor, a control member, and at least one marker on the surgical tool for determining an orientation and attitude of the surgical tool in relation to the visual image on the monitor. The image capturing device takes visual images of the articulating member. The monitor displays the visual images taken by the image capturing device. The control member operates and guides movement of the articulating member. The marker can be colors, symbols, letters, number, or in any combination thereof. An endoscope and a display may also be included.

15 Claims, 4 Drawing Sheets

(56) References Cited

U.S. PATENT DOCUMENTS

| | | | |
|---|---|---|---|
| 6,236,875 B1 | 5/2001 | Bucholz et al. | |
| 6,246,200 B1 | 6/2001 | Blumenkranz et al. | |
| 7,302,288 B1 | 11/2007 | Schellenberg | |
| 2005/0033117 A1* | 2/2005 | Ozaki | A61B 1/00009 |
| | | | 600/109 |
| 2006/0036163 A1 | 2/2006 | Viswanathan | |
| 2006/0100505 A1* | 5/2006 | Viswanathan | 600/424 |
| 2006/0139328 A1* | 6/2006 | Maki et al. | 345/161 |
| 2006/0258938 A1* | 11/2006 | Hoffman et al. | 600/424 |
| 2007/0021738 A1* | 1/2007 | Hasser | A61B 19/22 |
| | | | 606/1 |
| 2007/0032906 A1 | 2/2007 | Sutherland et al. | |
| 2007/0038080 A1 | 2/2007 | Salisbury, Jr. et al. | |
| 2007/0142849 A1 | 6/2007 | Ewers et al. | |
| 2007/0185377 A1* | 8/2007 | Murakami et al. | 600/106 |
| 2007/0208252 A1 | 9/2007 | Makower | |
| 2007/0249901 A1 | 10/2007 | Ohline et al. | |
| 2008/0009697 A1* | 1/2008 | Haider | A61B 17/14 |
| | | | 600/407 |
| 2009/0036902 A1* | 2/2009 | DiMaio et al. | 606/130 |
| 2009/0192519 A1* | 7/2009 | Omori | A61B 19/2203 |
| | | | 606/130 |

\* cited by examiner

MARKING ARTICULATING DIRECTION FOR SURGICAL INSTRUMENT

CROSS-REFERENCE TO RELATED APPLICATIONS

The present application claims priority to, and the benefit of, U.S. Provisional Application Ser. No. 61/154,202 filed Feb. 20, 2009, the entire contents of which is hereby incorporated by reference.

BACKGROUND

1. Technical Field

The present disclosure relates to an apparatus for determining the attitude of a surgical tool in relation to an image on a display. More particularly, the present disclosure relates to a surgical tool having markings placed about the distal region that correspond to markings placed about the controller. The markings provide the operator with the orientation of the surgical tool with respect to the image being displayed.

2. Background of the Related Art

Minimally invasive and laparoscopic procedures generally prevent a surgeon from directly observing an operation procedure. For such surgeries, the surgeon observes the procedure through an endoscope image projected on a monitor or a display. The display shows a surgical tool or instrument with respect to the surrounding anatomy of the patient. While watching the display the surgeon may not be observing the actual surgical tool or patient and may have to divert his attention during the procedure. As a result, the surgeon can lose or forget the orientation of the surgical tool with respect to the control unit while his attention is diverted from the display.

The surgeon must then reestablish the orientation of the surgical tool with respect to the control unit by trial and error. Thus, the surgeon moves the controller to determine the how and in which direction the surgical tool will respond. From this interaction, the surgeon can determine which specific directional movements of the control unit produces the desired results to the end of the surgical tool.

SUMMARY

Accordingly, the present disclosure provides a surgical apparatus with markings about a distal region, which will allow a surgeon to efficaciously determine the attitude of the articulating member, the required direction of movement, and move the controller in the corresponding direction. The surgical apparatus obviates the need for determining the attitude of the surgical tool by trial and error, moving the controller until the correct direction of movement is determined. One embodiment is directed to a surgical apparatus having markings about the distal region of the surgical tool and corresponding markings about a controller. In accordance with one aspect of the present disclosure, the surgical apparatus includes a surgical tool with an articulating member, an image capturing device, a display to show the image, a controller for controlling the movement of the articulating member, and indicia that indicate the attitude of the surgical tool in relation to the image on the display.

The indicia are a series of markers placed about the distal region of the surgical tool. A corresponding series of markers is also placed about the controller, which may be a knob. The markers may be a plurality of colors, symbols, numbers, or any combination thereof. Generally, the surgical tool is dimensioned for positioning within tissue and the image capturing device is an endoscope. The display and controller may be located on a separate console from the surgical tool.

In another embodiment, the surgical apparatus includes a surgical tool having an articulating member and a control member. The articulating member and the control member have a plurality of corresponding markers located about the periphery of each. Further, the articulating member and the control member are operatively connected such that moving the control member in the direction of one of the markers causes the articulating member to move in the direction of the corresponding maker, located about the distal region of the surgical tool.

The surgical apparatus includes an endoscope and a display. The display and control member are located on a console that is connected to the surgical tool and endoscope by a series of wires. The control member has markers surrounding a knob indicating possible directional movements of the articulating member. The markers may be a plurality of colors, symbols, letters, numbers, or any combination thereof.

BRIEF DESCRIPTION OF THE DRAWINGS

The accompanying drawings, which are incorporated in and constitute a part of this specification, illustrate embodiments of the disclosure, and together with a general description of the disclosure given above, and the detailed description of the embodiments given below, serve to explain the principles of the disclosure.

Other features and advantages of the present disclosure will become apparent from the following detailed description, taken in conjunction with the accompanying drawings, which illustrate, by way of example, the principles of the present disclosure.

DETAILED DESCRIPTION

The surgical apparatus of the present disclosure provides a quick reference system for a surgeon observing a surgical tool through a remote image. Moreover, the surgical apparatus allows the surgeon to determine the attitude of the surgical tool without having to move the surgical tool. The flexibility and inexpensive application of the present surgical apparatus greatly facilitates endoscopic surgery, where a variety of instruments can be used within an access portal and observed from a remote location.

The surgical apparatus contains a directional indicator so that during the surgical procedure so that manipulation of the surgical instrument in a particular direction can be knowingly performed by the surgeon. Specifically, the surgical apparatus greatly reduces the time spent determining the correct controller movement and risk of possible injury to the surgical sight. The disclosure is applied to a surgical tool having an articulating member, however may be applied to any surgical tool or instrument.

The attitude of a surgical tool can be determined by looking at the distal region of the surgical tool. Markings about the distal region of the surgical tool provide the surgeon with a visual reference to determine the side of the surgical tool being observed. The markings about the distal region of the surgical tool may be used in any type of surgical operation where the surgeon requires a quick indication as to the orientation of the instrument.

In the following description, as is traditional, the term "proximal" refers to the portion of the instrument closest to the operator while the term "distal" refers to the portion of the instrument remote from the operator.

Figure 1:
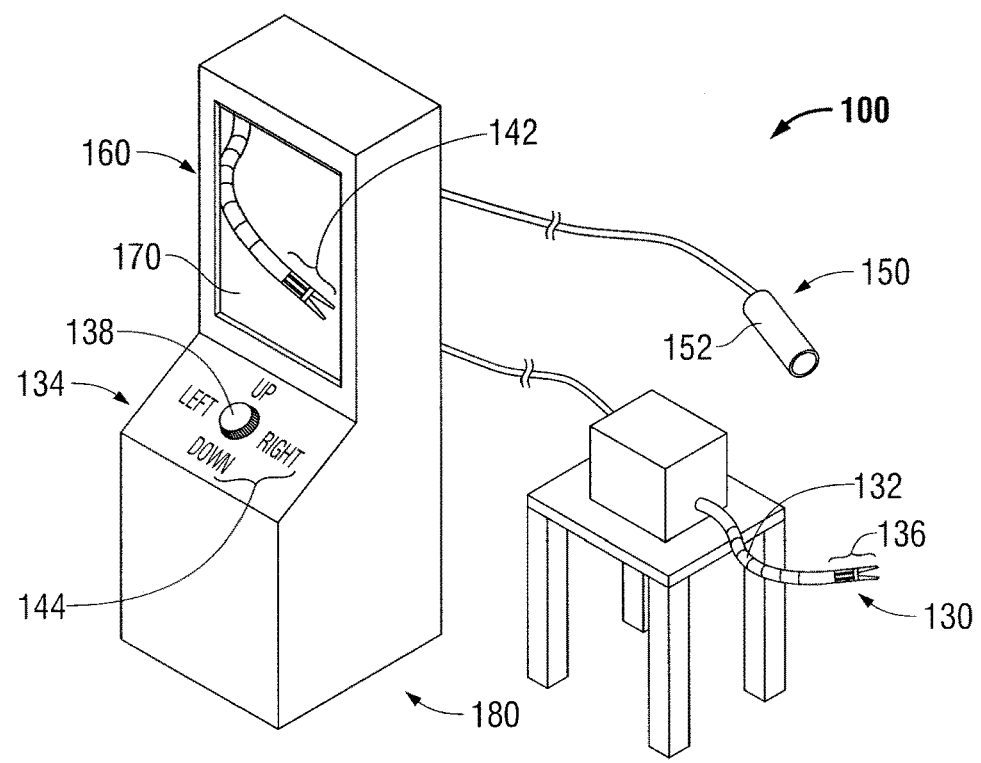
FIG. 1 is a view illustrating the surgical apparatus in accordance with the principles of the present disclosure.
Figure 2:
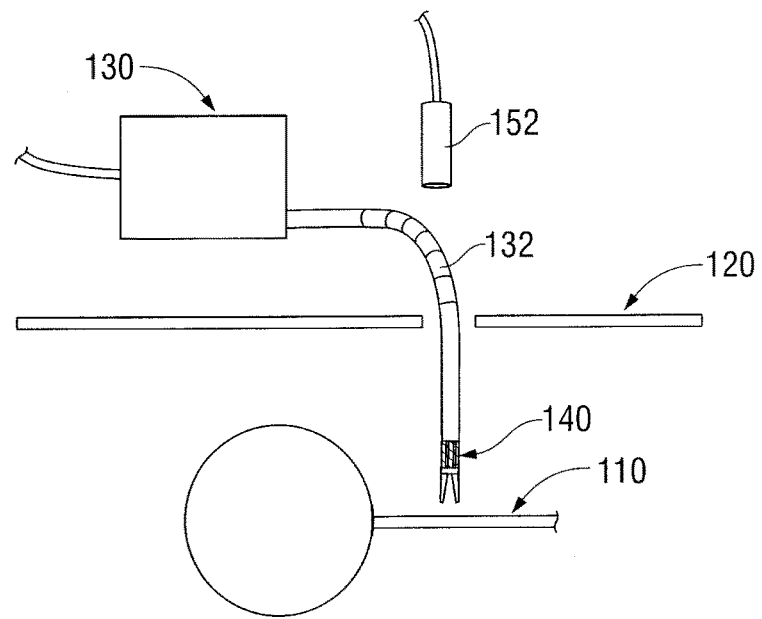
FIG. 2 is a perspective view of the surgical apparatus in accordance with the principles of the present disclosure.

Referring now to the drawings, in which like reference numerals identify identical or substantially similar parts throughout the several views, FIGS. 1-2 illustrate the surgical apparatus of the present disclosure. Surgical apparatus 100 can be any surgical instrument suitable for the performing a procedure in a body cavity. Surgical apparatus 100 is particularly adapted for use in laparoscopic surgery, where the peritoneal cavity is insufflated with a suitable gas, e.g., $CO_2$, to raise the cavity wall from the internal organs therein. A trocar assembly is then generally inserted through a penetration in the abdominal wall and instruments are inserted therethrough. An endoscope or other image capturing device is used to observe the instruments within the body cavity.

With reference to FIGS. 1-2, surgical apparatus 100 includes a surgical tool 130 and a controller 134. The surgical tool 130 generally has an articulating member 132 extending from a distal end of a housing. The articulating member has indicia 140 that indicate the attitude of the articulating member 132.

The indicia 140 comprise a first series of markings 142 placed about the distal region 136 of the articulating member 132. The controller 134 has a second series of markings 144 that correspond to the first series of markings 142. The controller 134 is configured to move the articulating member 132. Generally, the controller 134 is a movable handle (not shown) or a knob 138 that is designed to direct electrical currents to motors (not shown) in the surgical tool 130. The motors provide movement to the articulating member 132 by a mechanical connection. However, the knob 138 may also be mechanically connected to the articulating member 132 such that any movement of the knob 138 moves the articulating member 132 through a mechanical linkage system (no shown).

Generally, the surgeon observes the surgery from a display 160, which shows an image 170 taken from an image capturing device 150. During an endoscopic surgery the image capturing device 150 is an endoscope 152. The endoscope 152 may be a part of the surgical tool 130 or it may be a separate instrument. The display 160 and controller 134 may be combined into a single console 180 or they may be stand-alone units.

While observing the surgical tool 130 on the display 160, the surgeon is continually deciding which way to move the articulating member 132. The desired direction "A" of movement is determined by observing the distal region 136 of the articulating member 132 with respect to the surrounding anatomy 110 of the patient 120. The first series of markers 142 gives the surgeon a point of reference on the surgical tool 130, so that the surgeon can determine the attitude of the surgical tool 130 and determine the area of the surgical tool being observed.

The first series of markers 142 correspond to the second series of markers 144. The surgeon can then look at the second series of markers 144 placed about the periphery of the controller 134 to determine the orientation of the surgical tool 130 with respect to the controller 134. The controller 134 in can then be manipulated to produce the desired directional movement "A" of the articulating member 132.

Figure 3:
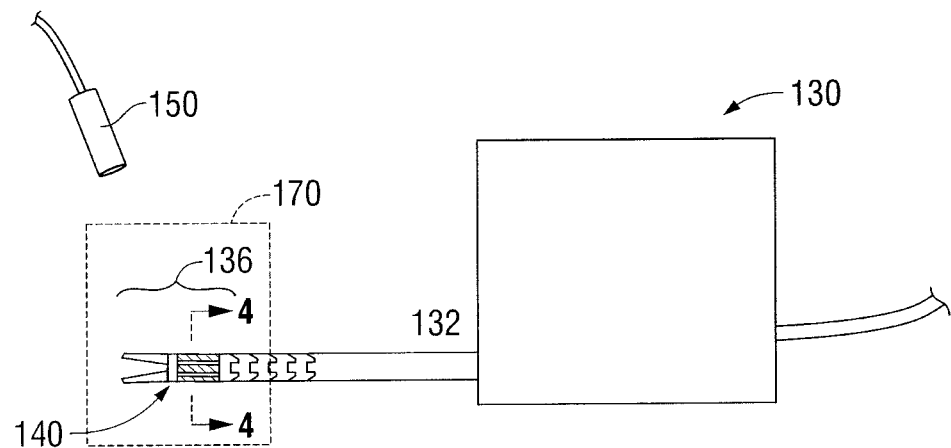
FIG. 3 is a view illustrating the surgical apparatus in accordance with the embodiment of FIGS. 1-2.
Figure 4:
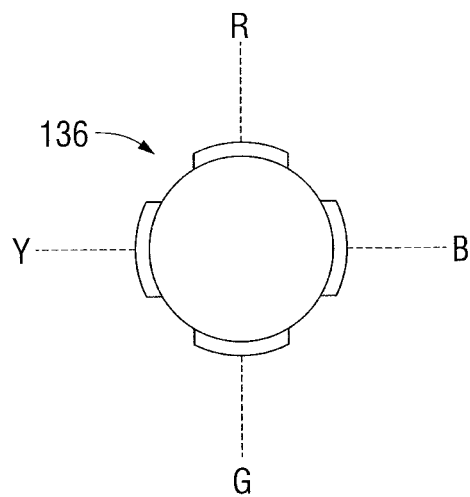
FIG. 4 is a front cross-sectional view of a distal region of an articulating member taken along section line 4-4 of FIG. 3.
Figure 5:
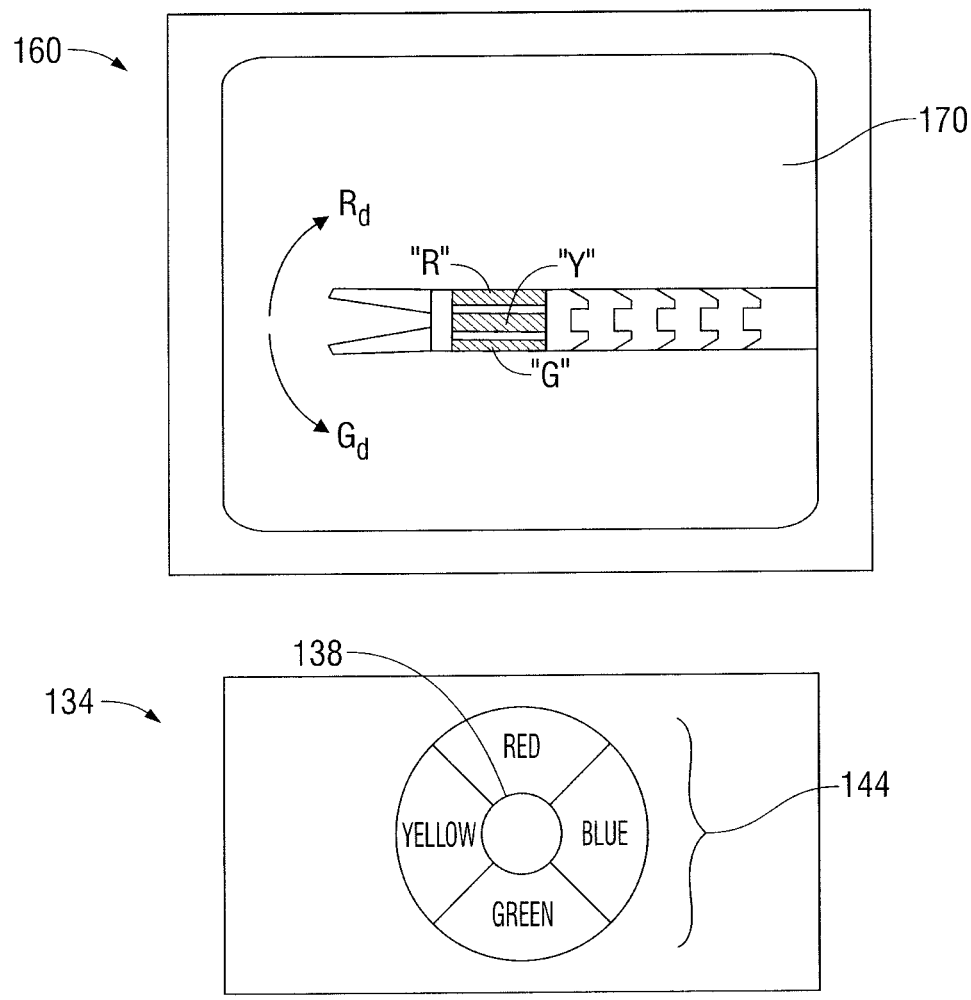
FIG. 5 is a view illustrating the display and controller in accordance with the embodiment of FIGS. 1-3.

The observation of any one marker on the distal region 136 provides the surgeon with the ability to orient the articulating member 132 with the controller 134 by looking at the second series of markings 144 and finding the same individual marking. The corresponding individual marking provides the surgeon with the orientation of the surgical tool 130 to the controller 134. For example, as illustrated in FIGS. 3-5, the corresponding markings were four colors, in the order of red 'R', blue 'B', green 'G', and yellow 'Y'. By observing the yellow marking on the distal end of the surgical tool 130 on the display 160, the surgeon can look at the yellow marker on the controller and determine which movements of the controller 134 will produce a desired result. Moving the controller 134 in the direction of the yellow marker will create a movement of the articulating member 132 that will bring the articulating member closer to the image capturing device 150. Moving the controller 134 to the marking immediately clockwise of the observed marking, in this case red, will produce a movement of the articulating member 132 in the direction of the arrow marked 'Rd'. Once the orientation is established, the surgeon can provide any directional command to the articulating member 132 in a predictable and repeatable manner.

Figure 6:
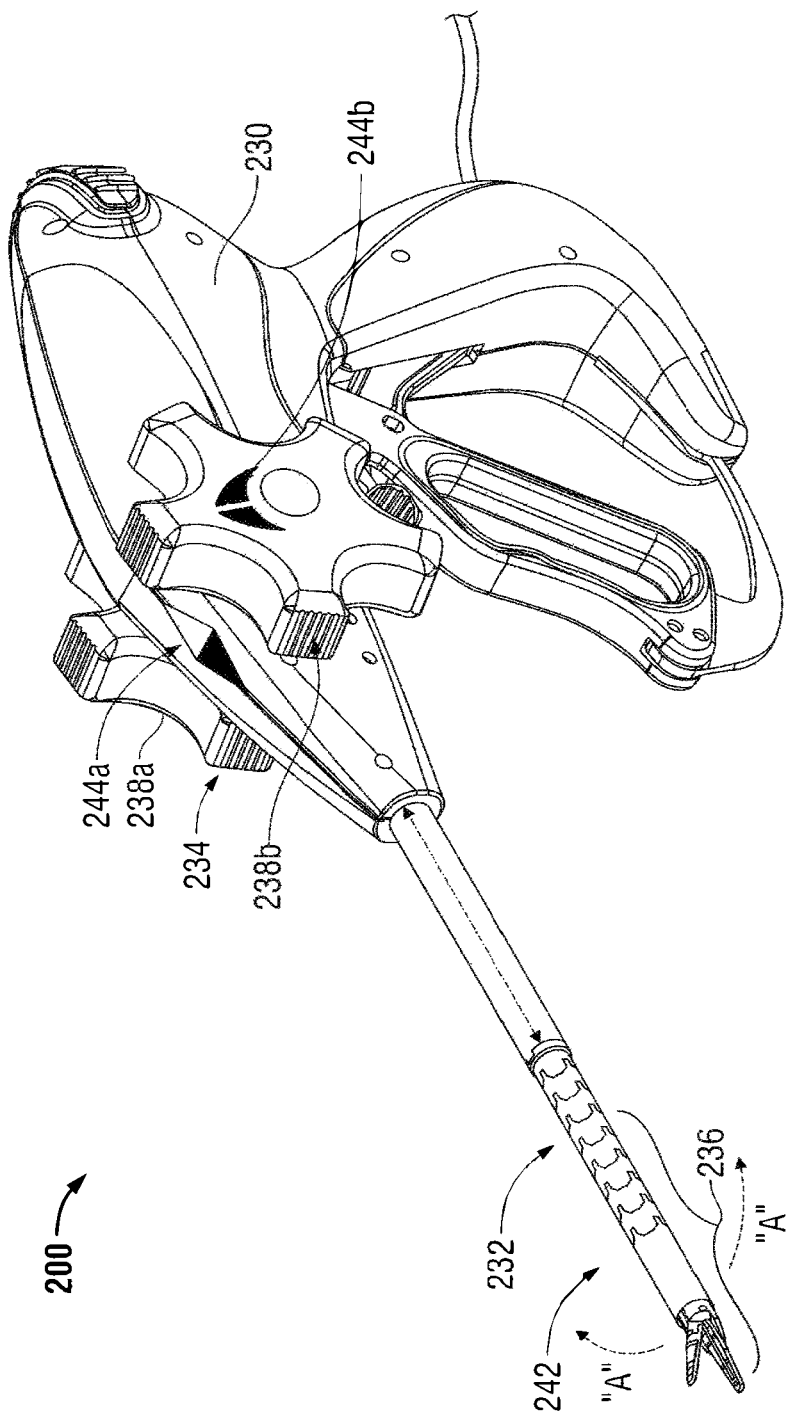
FIG. 6 is a perspective view of another embodiment of the surgical apparatus in accordance with the principles of the present disclosure.

In another embodiment, shown in FIG. 6, a surgical apparatus 200 is a surgical tool 230 having an articulating member 232 and a control member 234. The articulating member 232 has a first plurality of markers 242 located about a distal region 236. The first plurality of markers 242 defines a series of directional movements "A". The control member 234 is a plurality of knobs 238a and 238b having at least two corresponding second plurality of markers 244 located about the periphery of each of the knobs 238a and 238b. The control member 234 is configured such that when a knob 238a is displaced in the direction of one of the second plurality of markers 244a, the distal region 236 of the articulating member 232 moves in the direction defined by the corresponding marker of the first plurality of markers 242.

What is claimed:

1. A surgical apparatus for guiding movement of a surgical tool in relation to a surrounding anatomy of a patient, the surgical apparatus comprising:
   a surgical tool having an articulating member;
   an image capturing device configured to take a visual image of the articulating member;
   a monitor configured to display the visual image taken by the image capturing device;
   a control member in communication with the articulating member such that articulation of the control member operates and guides articulation of the articulating member;
   at least one first marker on the surgical tool for determining an orientation and attitude of the surgical tool in relation to the visual image on the monitor, the at least one first marker having a first indicium indicating a spatial direction; and at least one second marker placed about the control member, the at least one second marker having a second indicium corresponding to the first indicium, such that the at least one second marker provides an indication of an operation of the control member to guide the surgical tool in the spatial direction corresponding to the at least one first marker, wherein the orientation and attitude of the articulating member are defined by the first and second indicia and articulation of the articulating member is controlled by the control member acting on the articulating member independent of the visual image displayed on the monitor.

2. The surgical apparatus according to claim 1, wherein the at least one first marker is placed about a circumference of a distal region of the surgical tool.

3. The surgical apparatus according to claim 2, wherein the control member includes at least one knob, the at least one second marker placed about the at least one knob.

4. The surgical apparatus according to claim 3, wherein the respective first and second indicia of the at least one first and second markers are selected from the group consisting of colors, symbols, letters, numbers, and a combination thereof.

5. The surgical apparatus according to claim 1, wherein the image capturing device is an endoscope.

6. The surgical apparatus according to claim 1, wherein the control member is at a location remote from the surgical tool.

7. The surgical apparatus of claim 1, wherein the control member is configured to move the articulating member in the respective spatial direction indicated by the at least one first marker.

8. The surgical apparatus according to claim 1, wherein the surgical tool further includes a mechanical linkage system interconnected between the control member and the articulating member such that the control member articulates the articulating member via the mechanical linkage system.

9. The surgical apparatus according to claim 1, wherein the surgical tool further includes at least one motor, the at least one motor interconnected between the control member and the articulating member such that the control member articulates the articulating member via the at least one motor.

10. A surgical apparatus comprising:
a surgical tool having an articulating member, and a control member configured to control articulation of the articulating member, the control member in communication with the articulating member;
a first plurality of markers located about a distal region of the surgical tool, each marker of the first plurality of markers having a first indicium corresponding to one direction of a plurality of directions; and
a second plurality of markers located about the control member, wherein each marker of the second plurality of markers has a second indicium corresponding to the first indicium such that movement of the control member toward one marker of the second plurality of markers moves the articulating member in the direction of the corresponding marker of the first plurality of markers,
wherein the orientation and attitude of the articulating member are determined by the first and second indicia and articulation of the articulating member is controlled by the control member acting on the articulating member independent of a visual image of the articulating member.

11. The surgical apparatus of claim 10, further comprising:
an endoscope; and
a display.

12. The surgical apparatus according to claim 10, wherein the control member is at a remote location that is different from the surgical tool.

13. The surgical apparatus according to claim 10, wherein the control member having at least one knob.

14. The surgical apparatus according to claim 13, wherein located about the at least one knob is the second plurality of markers being color coded to correspond to the first plurality of markers being color strips placed about a distal region of the articulating member.

15. The surgical apparatus of claim 10, wherein the respective first and second indicia of the first and second pluralities of markers are selected from the group consisting of colors, symbols, letters, numbers, and a combination thereof.

* * * * *